US011776676B2

(12) United States Patent
Savolainen (10) Patent No.: US 11,776,676 B2
(45) Date of Patent: Oct. 3, 2023

(54) APPARATUS AND ASSOCIATED METHODS FOR DETERMINING EXERCISE SETTINGS

(71) Applicant: Nokia Technologies Oy, Espoo (FI)

(72) Inventor: Teemu Ilmari Savolainen, Nokia (FI)

(73) Assignee: Nokia Technologies Oy, Espoo (FI)

( * ) Notice: Subject to any disclaimer, the term of this patent is extended or adjusted under 35 U.S.C. 154(b) by 963 days.

(21) Appl. No.: 16/360,422

(22) Filed: Mar. 21, 2019

(65) Prior Publication Data

US 2019/0304584 A1 Oct. 3, 2019

(30) Foreign Application Priority Data

Mar. 27, 2018 (EP) ..................................... 18164415

(51) Int. Cl.
*G16H 20/30* (2018.01)
*G06N 20/00* (2019.01)
*A63B 24/00* (2006.01)
*A63B 22/06* (2006.01)

(52) U.S. Cl.
CPC ......... *G16H 20/30* (2018.01); *A63B 24/0062* (2013.01); *A63B 24/0075* (2013.01); *A63B 24/0087* (2013.01); *G06N 20/00* (2019.01); *A63B 22/0605* (2013.01); *A63B 2220/17* (2013.01); *A63B 2220/18* (2013.01); *A63B 2220/36* (2013.01); *A63B 2220/62* (2013.01); *A63B 2230/015* (2013.01); *A63B 2230/705* (2013.01)

(58) Field of Classification Search
CPC ................ G16H 20/30; A63B 24/0062; A63B 24/0075; A63B 24/0087; A63B 22/0605; A63B 2220/17; A63B 2220/18; A63B 2220/36; A63B 2220/62; A63B 2230/015; A63B 2230/705; G06N 20/00
See application file for complete search history.

(56) References Cited

U.S. PATENT DOCUMENTS

| 6,042,519 A | 3/2000 | Shea |
| 9,345,947 B2 | 5/2016 | Harris et al. |
| 2002/0045519 A1* | 4/2002 | Watterson .......... A63B 22/0023 482/54 |
| 2007/0219059 A1 | 9/2007 | Schwartz et al. |
| 2008/0077619 A1 | 3/2008 | Gilley et al. |

(Continued)

FOREIGN PATENT DOCUMENTS

| WO | 2015/038051 A1 | 3/2015 |
| WO | 2016/138042 A2 | 9/2016 |

OTHER PUBLICATIONS

"Fitness Machine", Bluetooth, Retrieved on Mar. 20, 2019, Webpage available at: https://www.bluetooth.com/specifications/gatt/viewer?attributeXmlFile=org.bluetooth.service.fitness_machine.xml.

(Continued)

*Primary Examiner* — Jeffrey S Vanderveen
(74) *Attorney, Agent, or Firm* — Harrington & Smith (57) ABSTRACT

An apparatus comprising means configured to:
determine, based on data representative of a current health state of a first user of a first exercise apparatus, settings for one or more exercise variables of the first exercise apparatus, wherein the settings are tailored to the first user's current health state; and
provide the determined settings for configuration of the first exercise apparatus.

19 Claims, 3 Drawing Sheets

(56) References Cited

U.S. PATENT DOCUMENTS

| | | | |
|---|---|---|---|
| 2011/0065549 A1* | 3/2011 | Jung | A63B 24/0062 |
| | | | 482/4 |
| 2013/0253943 A1 | 9/2013 | Lee et al. | |
| 2014/0045656 A1 | 2/2014 | Zhang | |
| 2015/0196805 A1 | 7/2015 | Koduri et al. | |
| 2015/0251074 A1* | 9/2015 | Ahmed | G06F 1/163 |
| | | | 700/91 |

OTHER PUBLICATIONS

"GATT Specifications", Bluetooth, Retrieved on Mar. 20, 2019, Webpage available at : https://www.bluetooth.com/specifications/gatt.

"GATT Services", Bluetooth, Retrieved on Mar. 20, 2019, Webpage available at : https://www.bluetooth.com/specifications/gatt/services.

"eGym Raises $45m Series C for Cloud-Connected Gym Equipment and Fitness Software", Techcrunch, Retrieved on Mar. 20, 2019, Webpage available at : https://techcrunch.com/2016/03/21/egym/.

Extended European Search Report received for corresponding European Patent Application No. 18164415.4, dated Oct. 9, 2018, 8 pages.

\* cited by examiner

APPARATUS AND ASSOCIATED METHODS FOR DETERMINING EXERCISE SETTINGS

TECHNICAL FIELD

The present disclosure relates to the tailoring of exercise settings for a first exercise apparatus based on the current health state of a first user. Some embodiments concern determining, based on data representative of the current health state of the first user, settings for one or more exercise variables of the first exercise apparatus, and providing the determined settings for configuration of the first exercise apparatus.

Some embodiments may relate to portable electronic devices, in particular, so-called hand-portable electronic devices which may be hand-held in use (although they may be placed in a cradle in use). Such hand-portable electronic devices include so-called Personal Digital Assistants (PDAs) and tablet PCs. The portable electronic devices/apparatus according to one or more disclosed example aspects/embodiments may provide one or more audio/text/video communication functions (e.g. tele-communication, video-communication, and/or text transmission, Short Message Service (SMS)/Multimedia Message Service (MMS)/emailing functions, interactive/non-interactive viewing functions (e.g. web-browsing, navigation, TV/program viewing functions), music recording/playing functions (e.g. MP3 or other format and/or (FM/AM) radio broadcast recording/playing), downloading/sending of data functions, image capture function (e.g. using a (e.g. in-built) digital camera), and gaming functions.

BACKGROUND

Research is currently being done to improve the functionality of exercise equipment.

The listing or discussion of a prior-published document or any background in this specification should not necessarily be taken as an acknowledgement that the document or background is part of the state of the art or is common general knowledge.

SUMMARY

According to a first aspect, there is provided an apparatus comprising means configured to:
determine, based on data representative of a current health state of a first user of a first exercise apparatus, settings for one or more exercise variables of the first exercise apparatus, wherein the settings are tailored to the first user's current health state; and
provide the determined settings for configuration of the first exercise apparatus.

The means may be configured to determine the settings for the one or more exercise variables to one or more of improve, and avoid deterioration of, the first user's current health state by use of the first exercise apparatus.

The means may be configured to determine the settings for the one or more exercise variables of the first exercise apparatus based on predefined settings or a machine learning algorithm.

The apparatus may comprise means configured to determine the current health state of the first user based on the data.

The means may be configured to determine the current health state of the first user based on predefined health states or a machine learning algorithm.

The apparatus may comprise means configured to:
determine which of a plurality of health states is most consistent with the data; and
obtain the settings for the one or more exercise variables, wherein the obtained settings correspond to the most consistent health state.

The data may comprise at least one of sleep measurements, vital sign measurements and activity measurements.

The data may comprise one or more measurements taken within the last 1 second, 10 seconds, 30 seconds, 1 minute, 5 minutes, 10 minutes, 15 minutes, 30 minutes, 1 hour, 6 hours, 12 hours, 24 hours or longer time period.

The sleep measurements may comprise measurements relating to at least the most recent sleep session of the first user.

The sleep measurements may comprise one or more of sleep duration, sleep quality, length of time since last sleep session and polysomnography measurements.

The vital sign measurements may comprise measurements taken immediately preceding use of the first exercise apparatus by the first user.

The vital sign measurements may comprise one or more of body temperature, blood pressure, heart rate, respiratory rate and pulse oximetry measurements.

The activity measurements may comprise measurements relating to a current exercise session of the first user.

The activity measurements may comprise one or more of exercise duration, step count, calories burned and length of time since last exercise.

The data may be indicative of one or more current health conditions of the first user.

The one or more current health conditions of the first user may comprise at least one of a short-term and chronic health condition.

The one or more current health conditions of the first user may comprise at least one of a physical health condition and a mental health condition.

The data may comprise one or more physical parameters of the first user.

The one or more physical parameters of the first user may comprise at least one of age, gender, weight, height, body fat percentage, body mass index and cholesterol level.

The apparatus may comprise means configured to receive the data representative of the current health state of the first user, and/or the one or more exercise variables of the first exercise apparatus, for use in determining the settings.

The data may be stored in a database comprising data for a plurality of different users of the first exercise apparatus, and, based on user identification information, the means may be configured to identify the first user among the plurality of different users, and receive, from the database, the data representative of the current health state of the first user for use in determining the settings.

The database may comprise one or more exercise variables for a plurality of different exercise apparatuses, and, based on exercise apparatus identification information, the means may be configured to identify the first exercise apparatus among the plurality of different exercise apparatuses, and receive, from the database, the one or more exercise variables for the first exercise apparatus for use in determining the settings.

The apparatus may comprise means configured to display or use the settings for configuration of the first exercise apparatus.

The apparatus may comprise means configured to one or more of monitor, provide, receive and store performance data for the first user following at least partial completion of an exercise using the first exercise apparatus configured with the settings.

The one or more exercise variables of the first exercise apparatus may comprise at least one of weight, resistance, number of repetitions, speed, inclination, seat height and duration.

The first exercise apparatus may be one or more of a treadmill, a cycling machine, a rowing machine, a cross trainer and a weights machine.

The apparatus may be one or more of an electronic device, a portable electronic device, a portable telecommunications device, a mobile phone, a personal digital assistant, a tablet, a phablet, a desktop computer, a laptop computer, a server, a smartphone, a smartwatch, smart eyewear, smart earwear, the first exercise apparatus, and a module for one or more of the same.

According to a further aspect, there is provided an apparatus comprising:
 at least one processor; and
 at least one memory including computer program code, the at least one memory and computer program code configured to, with the at least one processor, cause the apparatus at least to:
 determine, based on data representative of a current health state of a first user of a first exercise apparatus, settings for one or more exercise variables of the first exercise apparatus, wherein the settings are tailored to the first user's current health state; and
 provide the determined settings for configuration of the first exercise apparatus.

According to a further aspect, there is provided a computer-implemented method comprising:
 determining, based on data representative of a current health state of a first user of a first exercise apparatus, settings for one or more exercise variables of the first exercise apparatus, wherein the settings are tailored to the first user's current health state; and
 providing the determined settings for configuration of the first exercise apparatus.

The steps of any method disclosed herein do not have to be performed in the exact order disclosed, unless explicitly stated or understood by the skilled person.

Corresponding computer programs for implementing one or more steps of the methods disclosed herein are also within the present disclosure and are encompassed by one or more of the described example embodiments.

One or more of the computer programs may, when run on a computer, cause the computer to configure any apparatus, including a battery, circuit, controller, or device disclosed herein or perform any method disclosed herein. One or more of the computer programs may be software implementations, and the computer may be considered as any appropriate hardware, including a digital signal processor, a microcontroller, and an implementation in read only memory (ROM), erasable programmable read only memory (EPROM) or electronically erasable programmable read only memory (EEPROM), as non-limiting examples. The software may be an assembly program.

One or more of the computer programs may be provided on a computer readable medium, which may be a physical computer readable medium such as a disc or a memory device, or may be embodied as a transient signal. Such a transient signal may be a network download, including an internet download.

The present disclosure includes one or more corresponding aspects, example embodiments or features in isolation or in various combinations whether or not specifically stated (including claimed) in that combination or in isolation. Corresponding means for performing one or more of the discussed functions are also within the present disclosure.

The above summary is intended to be merely exemplary and non-limiting.

BRIEF DESCRIPTION OF THE FIGURES

A description is now given, by way of example only, with reference to the accompanying drawings, in which.

DESCRIPTION OF SPECIFIC ASPECTS/EMBODIMENTS

In the gym, users typically need to adjust the exercise variables for each exercise apparatus to suit their individual size and physical abilities. Examples of such exercise variables include weight, resistance, number of repetitions, speed, inclination, seat height and duration. Whilst it may be straightforward for a gym user to adjust certain exercise variables to suit their size (e.g. seat height), many are not aware of the optimum settings for their physical ability (e.g. weight, resistance, speed, etc). A user's physical ability is dictated by their current health and fitness, and although personal trainers can provide guidance in this regard, they usually do not have a detailed knowledge of the user's current health state. In some cases, the gym users themselves may not even be fully aware of their current health state. This lack of knowledge and consideration of a user's current health state puts them at risk of harming themselves through use of the exercise apparatus.

Furthermore, even if gym users were aware of the optimum settings for their individual physical abilities, the exercise variables for each exercise apparatus would still need to be manually configured. This may be particularly cumbersome, for example, in public gyms where a user may not be familiar with the gym equipment and/or where each exercise apparatus is often being configured for different people.

There will now be described an apparatus and associated methods that may address one or more of the above-mentioned issues.

Figure 1:
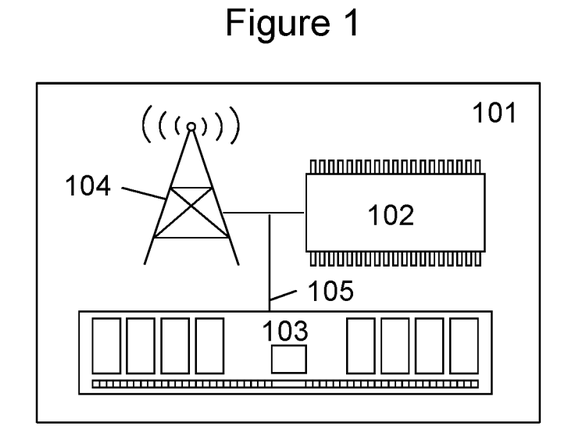
—
 FIG. 1 shows one example of the present apparatus.

FIG. 1 shows one example of the present apparatus 101. The apparatus 101 may be one or more of an electronic device, a portable electronic device, a portable telecommunications device, a mobile phone, a personal digital assistant, a tablet, a phablet, a desktop computer, a laptop computer, a server, a smartphone, a smartwatch, smart eyewear, smart earwear, an exercise apparatus, and a module for one or more of the same.

The apparatus 101 comprises means configured to: determine, based on data representative of a current health state of a first user of a first exercise apparatus, settings for one or more exercise variables of the first exercise apparatus; and provide the determined settings for configuration of the first exercise apparatus. In the example of FIG. 1, the means comprise a processor 102, memory 103 and transceiver 104 which are connected to one another via a data bus 105. The memory 103 includes computer program code which is configured to, with the processor 102, cause the apparatus 101 to perform the above-mentioned functionality.

The processor 102 may be configured for general operation of the apparatus 101 by providing signalling to, and receiving signalling from, the other components to manage their operation. The memory 103 may be configured to store computer code configured to perform, control or enable operation of the apparatus 101. The memory 103 may also be configured to store settings for the other components. The processor 102 may access the memory 103 to retrieve the component settings in order to manage the operation of the other components. The transceiver 104 may comprise a separate transmitter and receiver, and is configured to transmit data to, and receive data from, one or more other devices via a wired and/or wireless connection.

By implementing the present apparatus, the settings for the one or more exercise variables of the first exercise apparatus are tailored to the first user's current health state. This may help to improve, and/or avoid deterioration of, the first user's current health state by use of the first exercise apparatus.

Figure 2:
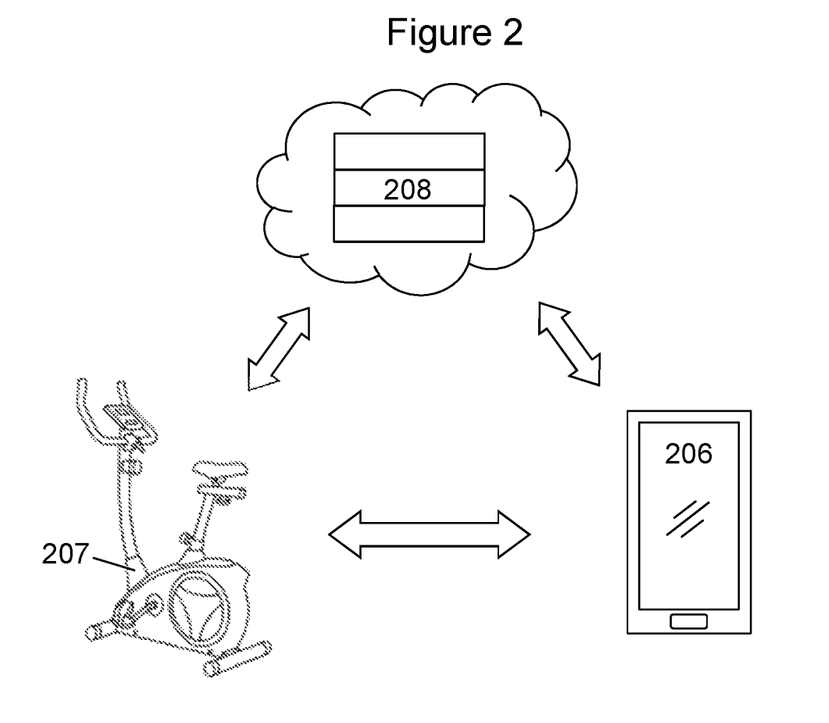
FIG. 2 shows a system comprising the present apparatus.

FIG. 2 shows a system comprising the first exercise apparatus 207, a user device 206 and a (cloud) server 208, which are configured to communicate with one another via one or more wired or wireless connections (e.g. Bluetooth, RFID, WiFi, ZigBee or ANT) as represented by the double-ended arrows. In this example, the present apparatus 101 forms part of the server 208, but as will be described later, it could form part of the first exercise apparatus 207 or user device 206 instead. Furthermore, although the first exercise apparatus 207 is shown here as a cycling machine, it could be a treadmill, rowing machine, cross trainer, weights machine or any other type of gym equipment.

The server 208 is configured to store data representative of the current health state of the first user, and may also be configured to store data representative of the current health state of one or more other users. The data may comprise at least one of sleep measurements, vital sign measurements and activity measurements. Furthermore, these measurements may be taken within the last 1 second, 10 seconds, 30 seconds, 1 minute, 5 minutes, 10 minutes, 30 minutes, 1 hour, 6 hours, 12 hours, or 24 hours or longer time period. Measurements older than 24 hours could be used to supplement more recent data in determining the current health state of the first user (e.g. taking into account longer term trends in certain data). Additionally or alternatively, measurements older than 24 hours could be used if more recent data is unavailable for some reason (e.g. privacy concern, communication error, no measurements, etc). In this case, the "current" health state may be assumed or inferred based on the one or more most recent measurements available.

The sleep measurements may comprise measurements relating to at least the most recent sleep session of the user, including one or more of sleep duration, sleep quality, length of time since last sleep session and polysomnography measurements. The vital sign measurements may comprise measurements taken immediately preceding use of the first exercise apparatus 207, including one or more of body temperature, blood pressure, heart rate, respiratory rate and pulse oximetry measurements. The activity measurements may comprise measurements relating to a current exercise session (i.e. workout) of the user, including one or more of exercise duration, step count, calories burned and length of time since last exercise.

Additionally or alternatively, the data representative of the current health state of a user may be indicative of one or more current health conditions or physical parameters of the user. The one or more current health conditions may comprise at least one of a short-term, chronic, physical and mental health condition, and the one or more physical parameters may comprise at least one of age, gender, weight, height, body fat percentage, body mass index and cholesterol level.

The data for each user may be sent to the server 208 by one or more recording devices for storage in a respective user account. For example, the data may be sent by an activity tracker (which may be the user device 206) worn by a user to monitor the number of steps walked, heart rate, quality of sleep, steps climbed, and/or other personal health and fitness metrics. The data could also be sent from a set of smart scales configured to monitor a user's weight, body fat percentage and/or body mass index amongst other physical parameters. Additionally or alternatively, a user's medical records may be sent from a device at a doctors surgery or hospital to the server 208. The data may be sent to the server 208 as and when it is generated (i.e. substantially in real-time), or it could be sent periodically, at pre-defined times, or whenever a connection between the recording device and server 208 becomes available.

The server 208 may also be configured to store exercise variables for the first exercise apparatus 207 and possibly one or more other exercise apparatuses. The exercise variables for each exercise apparatus are unlikely to change and should therefore only need to be sent to the server 208 once. The exercise variables for each exercise apparatus could be sent from the respective exercise apparatuses or from a central device which has access to this information.

In order to determine settings for the exercise variables of the first exercise apparatus 207 which are tailored to the current health state of the first user, the present apparatus 101 requires access to the data representative of the first user's current health state and the exercise variables of the first apparatus 207. The present apparatus 101 may therefore comprise means (e.g. transceiver 104) for receiving this information from the server 208 for use in determining the settings. The data representative of the current health state of each user, and the exercise variables for each exercise apparatus, would typically be stored within a database on the server 208. To access the relevant data sets, the means for receiving the information from the server 208 may be configured to identify the first user among the plurality of different users based on user identification information, and may be configured to identify the first exercise apparatus 207 amongst the plurality of different exercise apparatuses based on exercise apparatus identification information. Once the first user and first exercise apparatus 207 have been identified (e.g. as part of a data query sent to the database), the means for receiving is able to receive the data representative of the current health state of the first user and the exercise variables of the first exercise apparatus 207 for use in determining the settings.

As part of the determination of settings for the one or more exercise variables, the apparatus 101 may comprise means (e.g. the processor 102, memory 103 and code described in relation to FIG. 1) configured to determine the current health state of the first user based on the data. The means configured to determine the current health state may be configured to determine which of a plurality of health states is most consistent with the data, and then obtain settings which correspond to the most consistent health state. This may be achieved based on predefined health states or a machine learning algorithm. For example, a plurality of predefined health states may be stored within a database on the server 208 together with one or more health measurements or traits typically associated with those particular health states. In this scenario, the means configured to determine the current health state would compare the data representative of the current heath state of the first user against the health measurements or traits associated with each predefined health state to determine the most consistent health state. Alternatively, the means configured to determine the current health state may be configured to recognise a particular health state by analysing the data representative of the current health state using previously acquired knowledge. For example, the means may recognise that the first user is at a higher risk of heart attack or cardiac arrest relative to an average gym user based on one or more of his/her heart rate, blood pressure, cholesterol level and medical history.

The predefined or recognised health states could be defined in many different ways. For instance, there could be a plurality of health states each having a different associated risk of health deterioration caused by use of the first exercise apparatus 207. In this case, deterioration of the first user's current health state may be any temporary, permanent or semi-permanent physical or mental damage to the user. Additionally or alternatively, each health state may be associated with a different medical condition or group of medical conditions. For example, all gym users with a cardiovascular disease may fall within a first health state and all gym users with a respiratory disease may fall within a second health state. Regardless of how the different health states are defined, each health state would have corresponding settings for the one or more exercise variables of the first exercise apparatus 207 which are suitable for that particular health state.

Similar to the determination of the current health state of the first user, determination of the settings for the one or more exercise variables could also be achieved based on predefined data (settings) or a machine learning algorithm. For example, the settings corresponding to each predefined health state may be predefined and stored in a database together with the predefined health states. In this way, the means (e.g. the processor 102, memory 103 and code described in relation to FIG. 1) configured to determine the settings for the one or more exercise variables would simply need to obtain the corresponding settings from the database once the current health state of the first user has been determined. If a greater degree of tailoring was required (e.g. due to the potentially large number of different possible health states), however, a machine learning algorithm could be used to calculate appropriate settings rather than using predefined settings for each health state.

The predefined or calculated settings for the one or more exercise variables may be determined based on advice from one or more reliable medical practitioners (e.g. doctor or nurse) or information from reliable medical publications (e.g. books, websites or journals). Advice from any medical practitioners would typically need to be obtained in advance, but information from medical publications could be obtained substantially in real-time. This aspect may be more important if the first user is suffering from a current health condition rather than merely experiencing tiredness due to lack of sleep or previous exercise.

Figure 3:
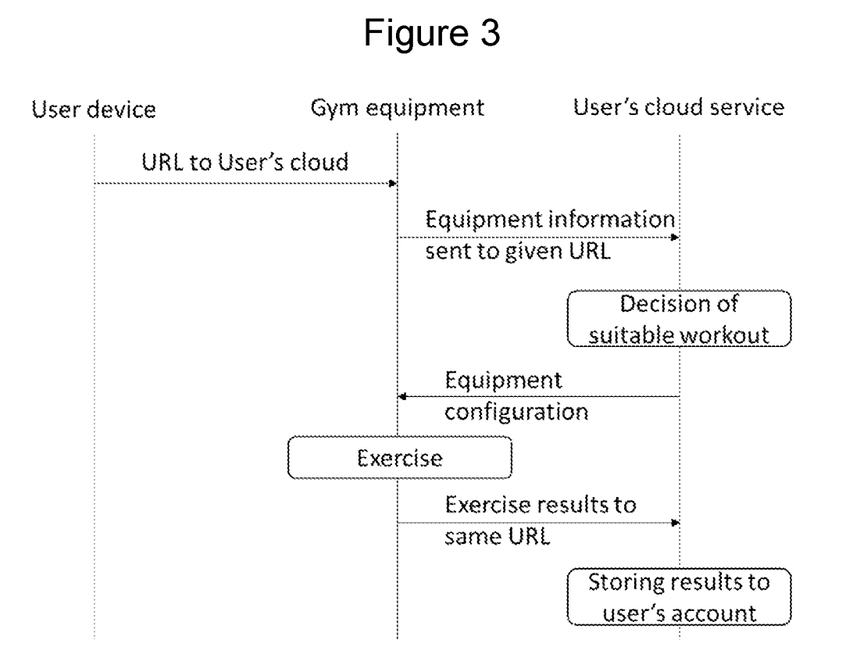
FIG. 3 shows one example of data flow for the system of FIG. 2.

FIG. 3 shows one example of data flow for the system of FIG. 2. First, the user device 206 and first gym apparatus 207 ("gym equipment") detect and connect to one another. Once connected, the user device 206 sends user identification information to the first exercise apparatus 207 in the form of a uniform resource locator (URL) which directs the first exercise apparatus 207 to the first user's account on the server 208 ("user's cloud service"). The first exercise apparatus 207 then sends equipment information to the URL. The equipment information may simply comprise exercise apparatus identification information such as a code which identifies the type, make and model of the first exercise apparatus 207, or it may comprise the one or more exercise variables. In the former scenario, the server 208 could determine the exercise variables using the exercise apparatus identification information (e.g. by querying an internal or external database). On receipt of the equipment information, the server 208 is able to obtain the data representative of the current health state of the first user from the URL, and determine the settings for the one or more exercise variables of the first exercise apparatus 207 ("equipment configuration") based on this data. The settings for the one or more exercise variables are then sent from the server 208 to the first exercise apparatus 207 for configuration thereof.

Configuration of the first exercise apparatus 207 may be performed manually by the first user or automatically by the first exercise apparatus 207. In the former scenario, the first exercise apparatus 207 may be configured to display the settings for the one or more exercise variables on a graphical user interface so that the first user knows how to configure the first exercise apparatus 207. In the latter scenario, the first exercise apparatus 207 would be configured to use the settings to configure itself. Either way, the first user is then able to use the first exercise apparatus as configured.

As shown, the first exercise apparatus 207 may also be configured to monitor the first user's performance as he/she exercises, and send performance data following at least partial completion of the exercise by the first user to the user's account on the server 208 via the same URL as before. The performance data may be sent to the user's account in real-time as it is generated. In some cases, the first exercise apparatus 207 may also be configured to display the performance data on a graphical user interface during and/or after at least partial completion of the exercise. Performance data generated earlier in the current exercise could be used to influence the settings of the first exercise apparatus 207 later in the same exercise (e.g. the settings could be changed dynamically).

Furthermore, performance data generated at any point during the current exercise could be used to influence the settings of one or more other exercise apparatuses used by the first user later in the same workout session.

Access to the user's account could be provided in ways other than URL depending on implementation. For example, a user certificate or simple user identifier could be used instead provided that the first exercise apparatus 207 has the relevant means to use the information (e.g. is in communication with a fixed vendor specific cloud server that stores the user identification).

In the example of FIG. 3, the user device 206 could simply be the first user's gym pass (e.g. in the form of a card or wristband) provided that it is able to send user identification information to the first exercise apparatus 207. Nevertheless, the user device 206 could be a more sophisticated device such as a smartphone, smartwatch, smart eyewear or smart earbuds.

Figure 4:
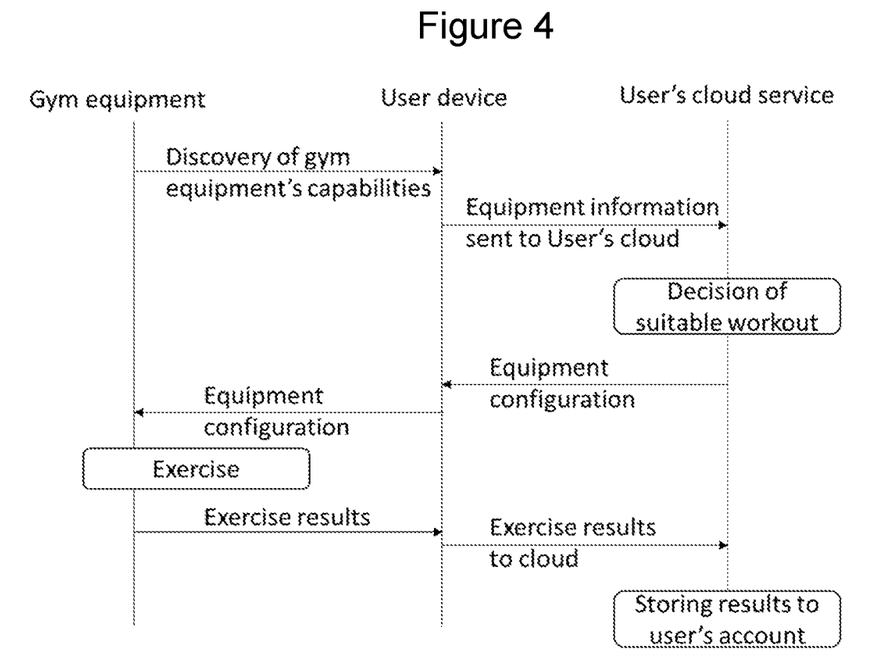
FIG. 4 shows another example of data flow for the system of FIG. 2.

FIG. 4 shows another example of data flow for the system of FIG. 2. As before, the user device 206 and first exercise apparatus 207 ("gym equipment") detect and connect to one another. Unlike the previous example, however, the first exercise apparatus 207 then sends equipment information ("equipment's capabilities") to the user device 206 which is subsequently forwarded by the user device 206 to the first user's account on the server 208 ("user's cloud service"). On receipt of the equipment information, the server 208 determines the settings for the one or more exercise variables of the first exercise apparatus 207 ("equipment configuration") as before and sends the settings to the user device 206. The user device 206 then forwards the settings to the first exercise apparatus for configuration thereof. Once the exercise has been at least partially completed by the first user, the associated performance data is sent from the first exercise apparatus 207 to the user device 206 and forwarded to the server 208 for storage in the first user's account.

Although this example requires the use of a more sophisticated user device 206 (e.g. smartphone rather than gym pass), it does not require the first exercise apparatus 207 to be connected to the server 208 and avoids the need for the user device 206 to provide user identification information to the first exercise apparatus 207 (which improves privacy and security).

Figure 5:
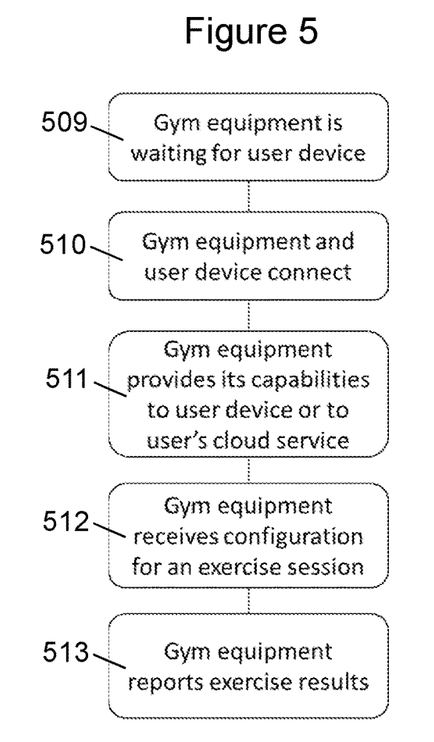
FIG. 5 shows a flowchart from the perspective of the first exercise apparatus.

FIG. 5 shows a flowchart from the perspective of the first exercise apparatus ("gym equipment") based on the examples of FIGS. 3 and 4. As shown, the first exercise apparatus waits for 509 and connects to 510 the user device. Once connected, it then provides 511 the one or more exercise variables ("capabilities") to either the user device or directly to the server ("user's cloud service").

The first exercise apparatus subsequently receives 512 the settings for the one or more exercise variables ("configuration"), is configured with the settings, and later provides 513 the performance data ("exercise results") to the user device or server.

Figure 6:
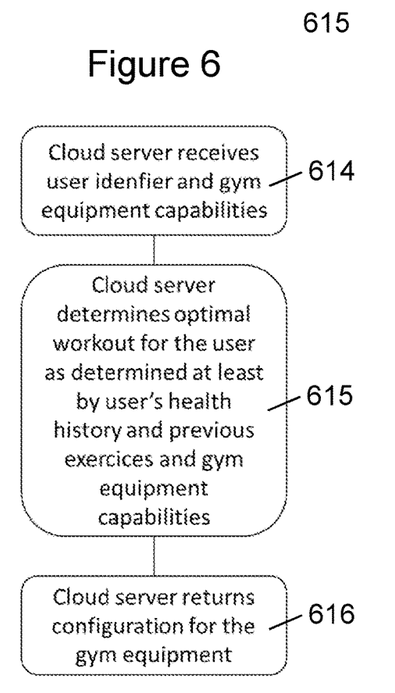
FIG. 6 shows a flowchart from the perspective of the cloud server.

FIG. 6 shows a flowchart from the perspective of the server ("cloud server") based on the examples of FIGS. 3 and 4. As shown, the server receives 614 the user identification information ("user identifier") and one or more exercise variables ("gym equipment capabilities") from either the user device or first exercise apparatus, and determines 615 the settings ("optimal workout") for the one or more exercise variables based on the data representative of the current health state of the first user ("user's health history and previous exercises") and the one or more exercise variables. The determined settings are then sent 616 from the server to the user device or first exercise apparatus for configuration of the first exercise apparatus.

In each of the examples described above, determination of the settings for the one or more exercise variables of the first apparatus is performed by the server. In other examples, however, this functionality could be performed by the user device or first exercise apparatus provided they have sufficient processing power. For example, the user device may store, or have access to, the data representative of the first user's health state and the exercise variables for at least the first exercise apparatus. In this scenario, the user device may be configured to receive exercise apparatus identification information from the first exercise apparatus and determine the settings for the one or more exercise variables itself. Alternatively, rather than storing or having access to the exercise variables, the user device could receive the exercise variables from the first exercise apparatus instead of the exercise apparatus identification information.

Similarly, the first exercise apparatus may be configured to receive user identification information from the user device, access data representative of the first user's current health state from the server using the user identification information, and determine the settings for the one or more exercise variables itself. Alternatively, the first exercise apparatus could receive the data representative of the first user's current health state from the user device instead of the user identification information.

Figure 7:
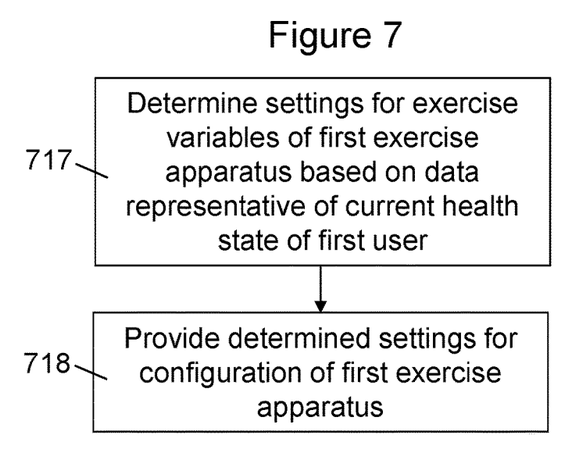
FIG. 7 shows a flowchart illustrating a method of using the present apparatus.

FIG. 7 shows the main steps 717-718 of a method of using the present apparatus. The method generally comprises: determining, based on data representative of a current health state of a first user of a first exercise apparatus, settings for one or more exercise variables of the first exercise apparatus, wherein the settings are tailored to the first user's current health state 717; and providing the determined settings for configuration of the first exercise apparatus 718.

Figure 8:
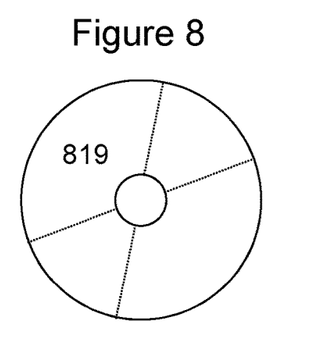
FIG. 8 shows a computer-readable medium comprising a computer program configured to perform, control or enable a method described herein.

FIG. 8 illustrates schematically a computer/processor readable medium 819 providing a computer program according to one embodiment. The computer program may comprise computer code configured to perform, control or enable one or more of the method steps 717-718 of FIG. 7 using at least part of the apparatus described herein. In this example, the computer/processor readable medium 819 is a disc such as a digital versatile disc (DVD) or a compact disc (CD). In other embodiments, the computer/processor readable medium 819 may be any medium that has been programmed in such a way as to carry out an inventive function. The computer/processor readable medium 819 may be a removable memory device such as a memory stick or memory card (SD, mini SD, micro SD or nano SD).

Other embodiments depicted in the figures have been provided with reference numerals that correspond to similar features of earlier described embodiments. For example, feature number 1 can also correspond to numbers 101, 201, 301 etc. These numbered features may appear in the figures but may not have been directly referred to within the description of these particular embodiments. These have still been provided in the figures to aid understanding of the further embodiments, particularly in relation to the features of similar earlier described embodiments.

It will be appreciated to the skilled reader that any mentioned apparatus/device and/or other features of particular mentioned apparatus/device may be provided by apparatus arranged such that they become configured to carry out the desired operations only when enabled, e.g. switched on, or the like. In such cases, they may not necessarily have the appropriate software loaded into the active memory in the non-enabled (e.g. switched off state) and only load the appropriate software in the enabled (e.g. on state). The apparatus may comprise hardware circuitry and/or firmware. The apparatus may comprise software loaded onto memory. Such software/computer programs may be recorded on the same memory/processor/functional units and/or on one or more memories/processors/functional units.

In some embodiments, a particular mentioned apparatus/device may be pre-programmed with the appropriate software to carry out desired operations, and wherein the appropriate software can be enabled for use by a user downloading a "key", for example, to unlock/enable the software and its associated functionality. Advantages associated with such embodiments can include a reduced requirement to download data when further functionality is required for a device, and this can be useful in examples where a device is perceived to have sufficient capacity to store such pre-programmed software for functionality that may not be enabled by a user.

It will be appreciated that any mentioned apparatus/circuitry/elements/processor may have other functions in addition to the mentioned functions, and that these functions may be performed by the same apparatus/circuitry/elements/processor. One or more disclosed aspects may encompass the electronic distribution of associated computer programs and computer programs (which may be source/transport encoded) recorded on an appropriate carrier (e.g. memory, signal).

It will be appreciated that any "computer" described herein can comprise a collection of one or more individual processors/processing elements that may or may not be located on the same circuit board, or the same region/position of a circuit board or even the same device. In some embodiments one or more of any mentioned processors may be distributed over a plurality of devices. The same or different processor/processing elements may perform one or more functions described herein.

It will be appreciated that the term "signalling" may refer to one or more signals transmitted as a series of transmitted and/or received signals. The series of signals may comprise one, two, three, four or even more individual signal components or distinct signals to make up said signalling. Some or all of these individual signals may be transmitted/received simultaneously, in sequence, and/or such that they temporally overlap one another.

With reference to any discussion of any mentioned computer and/or processor and memory (e.g. including ROM, CD-ROM etc), these may comprise a computer processor, Application Specific Integrated Circuit (ASIC), field-programmable gate array (FPGA), and/or other hardware components that have been programmed in such a way to carry out the inventive function.

The applicant hereby discloses in isolation each individual feature described herein and any combination of two or more such features, to the extent that such features or combinations are capable of being carried out based on the present specification as a whole, in the light of the common general knowledge of a person skilled in the art, irrespective of whether such features or combinations of features solve any problems disclosed herein, and without limitation to the scope of the claims. The applicant indicates that the disclosed aspects/embodiments may consist of any such individual feature or combination of features. In view of the foregoing description it will be evident to a person skilled in the art that various modifications may be made within the scope of the disclosure.

While there have been shown and described and pointed out fundamental novel features as applied to different embodiments thereof, it will be understood that various omissions and substitutions and changes in the form and details of the devices and methods described may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment may be incorporated in any other disclosed or described or suggested form or embodiment as a general matter of design choice. Furthermore, in the claims means-plus-function clauses are intended to cover the structures described herein as performing the recited function and not only structural equivalents, but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

The invention claimed is:

1. An apparatus comprising:
   at least one processor; and
   at least one non-transitory memory including computer program code; the at least one non-transitory memory storing instructions, that when executed by the at least one processor, cause the apparatus at least to perform:
   receiving by a first exercise apparatus from a user device of a first user identification information comprising a uniform resource locator directing the first exercise apparatus to an account of the first user on a server;
   based on the uniform resource locator, receiving data comprising user identification information for the first user of the first exercise apparatus,
   wherein the data is received from a database comprising data of one or more exercise variables for a plurality of different users of a plurality of different exercise apparatuses,
   wherein exercise variables for each exercise apparatus of the plurality of different exercise apparatuses are received at the database from each respective exercise apparatus via a central device, and
   wherein the one or more exercise variables for the plurality of different exercise apparatuses are generated in real time, periodically, or at pre-defined times;
   identifying in the database the first exercise apparatus among the plurality of different exercise apparatuses;
   based on the identifying, receiving from the database information comprising an indication of one or more exercise variables and data representative of the current health state of the first user for use in determining the settings,
   wherein the determining comprises comparing by first exercise apparatus data representative of the first user's current health state during partial completion of an exercise being performed on the first exercise apparatus against a plurality of predefined health states of the first user caused by the first exercise apparatus and detected by the first exercise apparatus to identify a predefined health state of the plurality of predefined health states that is most consistent with the first user's current health state, wherein each of the predefined health states has a different associated risk of health deterioration of the first user's current health state;
   based on the comparing identifying an associated risk of health deterioration of the first user's current health state, obtain from a list of medical publications information for determining predefined or calculated settings for one or more exercise variables;
   determining, based on the identifying and on the information from the list of medical publications, settings for one or more exercise variables of the first exercise apparatus; and
   based on the determining, changing a configuration of the first exercise apparatus comprising adjusting during the exercise settings of one or more exercise variables of the first exercise apparatus to the first user's current health state.

2. The apparatus of claim 1, wherein the at least one non-transitory memory is storing instructions executed by the at least one processor, to cause the apparatus at least to perform: determining which of a plurality of health states is most consistent with the data; and obtaining the settings for the one or more exercise variables, wherein the obtained settings correspond to the most consistent health state.

3. The apparatus of claim 1, wherein the sleep measurements comprise one or more of: sleep duration; sleep quality; length of time since last sleep session; or polysomnography measurements.

4. The apparatus of claim 1, wherein the data further comprises at least one of vital sign measurements or activity measurements.

5. The apparatus of claim 4, wherein the activity measurements comprise measurements relating to a current exercise session of the first user.

6. The apparatus of claim 1, wherein the data is indicative of one or more current health conditions of the first user.

7. The apparatus of claim 1, wherein the data comprises one or more physical parameters of the first user.

8. The apparatus of claim 1, wherein
the at least one non-transitory memory is storing instructions executed by the at least one processor, to cause the apparatus at least to perform:
upon connection of the user device, receiving user identification information of the first exercise apparatus in the form of the uniform resource locator which directs the first exercise apparatus to the first user's account on a user's cloud service; and
sending equipment information to the uniform resource locator, wherein the equipment information comprises exercise apparatus identification information code which identifies a type, make, and model of the first exercise apparatus.

9. The apparatus of claim 1, wherein the data is received at the database via the central device from an activity tracker worn by the first user, wherein the data comprises information comprising a number of steps walked, heart rate, quality of sleep, steps climbed, or other personal health and fitness metrics, received from a set of smart scales configured to monitor a user's weight, body fat percentage or body mass index amongst physical parameters, or information received from a user's medical records via a device at a doctors office.

10. The apparatus of claim 1, wherein the apparatus is embodied in one of a gym pass or wristband for the first user.

11. The apparatus of claim 1, wherein the at least one non-transitory memory is storing instructions executed by the at least one processor, to cause the apparatus at least to perform:
displaying or using the settings for the change of configuration of the first exercise apparatus.

12. The apparatus of claim 1, wherein the at least one non-transitory memory is storing instructions executed by the at least one processor, to cause the apparatus at least to perform:
one or more of monitoring, providing, receiving or storing performance data for the first user following at least partial completion of an exercise using the first exercise apparatus configured with the settings.

13. The apparatus of claim 1, wherein the at least one non-transitory memory is storing instructions executed by the at least one processor, to cause the apparatus at least to perform:
determining the settings for the one or more exercise variables of the first exercise apparatus based on predefined settings or a machine learning algorithm.

14. The apparatus of claim 1, wherein the at least one non-transitory memory is storing instructions executed by the at least one processor, to cause the apparatus at least to perform:
determining the current health state of the first user based on the data.

15. The apparatus of claim 1, wherein the at least one non-transitory memory is storing instructions executed by the at least one processor, to cause the apparatus at least to perform:
determining the current health state of the first user based on predefined health states or a machine learning algorithm.

16. The apparatus of claim 1, wherein the vital sign measurements comprise measurements taken immediately preceding use of the first exercise apparatus by the first user.

17. The apparatus of claim 1, wherein the one or more exercise variables of the first exercise apparatus comprise at least one of weight, resistance, number of repetitions, speed, inclination, seat height or duration.

18. A computer-implemented method comprising:
receiving by a first exercise apparatus from a user device of a first user identification information comprising a uniform resource locator directing the first exercise apparatus to an account of the first user on a server;
based on the uniform resource locator, receiving data comprising user identification information for the first user of the first exercise apparatus,
wherein the data is received from a database comprising data of one or more exercise variables for a plurality of different users of a plurality of different exercise apparatuses,
wherein exercise variables for each exercise apparatus of the plurality of different exercise apparatuses are received at the database from each respective exercise apparatus via a central device, and
wherein the one or more exercise variables for the plurality of different exercise apparatuses are generated in real time, periodically, or at pre-defined times;
identifying in the database the first exercise apparatus among the plurality of different exercise apparatuses;
based on the identifying, receiving from the database information comprising an indication of one or more exercise variables and data representative of the current health state of the first user for use in determining the settings;
determining, based on data representative of a current health state of the first user of the first exercise apparatus, settings for one or more exercise variables of the first exercise apparatus,
wherein the determining comprises comparing by the first exercise apparatus data representative of the first user's current health state during partial completion of an exercise being performed on the first exercise apparatus against health measurements associated with at least one of a plurality of predefined health states of the first user caused by the first exercise apparatus and detected by the first exercise apparatus to identify a predefined health state of the plurality of predefined health states that is most consistent with the first user's current health state, wherein each of the predefined health states has a different associated risk of health deterioration of the first user's current health state;
based on the comparing identifying an associated risk of health deterioration of the first user's current health state, obtain from a list of medical publications information for determining predefined or calculated settings for one or more exercise variables; and based on the identifying and on the information from the list of medical publications, changing configuration of the first exercise apparatus comprising adjusting during the exercise settings of one or more exercise variables of the first exercise apparatus to the first user's current health state.

19. A non-transitory computer readable medium comprising program instructions stored thereon for performing at least:

receiving by a first exercise apparatus from a user device of a first user identification information comprising a uniform resource locator directing the first exercise apparatus to an account of the first user on a server;

based on the uniform resource locator, receiving data comprising user identification information for the first user of the first exercise apparatus, wherein the data is received from a database comprising data of one or more exercise variables for a plurality of different users of a plurality of different exercise apparatuses, wherein exercise variables for each exercise apparatus of the plurality of different exercise apparatuses are received at the database from each respective exercise apparatus via a central device, and wherein the one or more exercise variables for the plurality of different exercise apparatuses are generated in real time, periodically, or at pre-defined times;

identifying in the database the first exercise apparatus among the plurality of different exercise apparatuses;

based on the identifying, receiving from the database information comprising an indication of one or more exercise variables and data representative of the current health state of the first user for use in determining the settings determining, based on data representative of a current health state of the first user of the first exercise apparatus, settings for one or more exercise variables of the first exercise apparatus, wherein the settings are tailored to the first user's current health state, wherein the determining comprises comparing by the first exercise apparatus data representative of the first user's current health state during partial completion of an exercise being performed on the first exercise apparatus against health measurements associated with at least one of a plurality of predefined health states of the first user caused by the first exercise apparatus and detected by the first exercise apparatus to identify a predefined health state of the plurality of predefined health states that is most consistent with the first user's current health state, wherein each of the predefined health states has a different associated risk of health deterioration of the first user's current health state;

based on the comparing identifying an associated risk of health deterioration of the first user's current health state, obtain from a list of medical publications information for determining predefined or calculated settings for one or more exercise variables; and based on the identifying and on the information from the list of medical publications, changing configuration of the first exercise apparatus to cause comprising adjusting during the exercise settings of one or more exercise variables of the first exercise apparatus to the first user's current health state.

* * * * *